US005559026A

United States Patent [19]

Price et al.

[11] Patent Number: 5,559,026
[45] Date of Patent: Sep. 24, 1996

[54] GENES ENCODING A NOVEL FAMILY OF POTASSIUM CHANNELS

[75] Inventors: Laura A. Price, Langhorne, Pa.; Mark H. Pausch, Robbinsville, N.J.

[73] Assignee: American Cyanamid Company, Madison, N.J.

[21] Appl. No.: 332,312

[22] Filed: Oct. 31, 1994

[51] Int. Cl.[6] .............................. C12N 1/14; C12N 15/00; C07H 21/04
[52] U.S. Cl. .................................... 435/254.2; 435/320.1; 536/23.5
[58] Field of Search .............................. 435/254.2, 320.1; 536/23.5

[56] References Cited

U.S. PATENT DOCUMENTS

| | | | |
|---|---|---|---|
| 5,356,775 | 10/1994 | Hebert et al. | 435/6 |
| 5,492,825 | 2/1996 | Jan et al. | 435/240.2 |
| 5,494,895 | 2/1996 | Garcia et al. | 514/12 |

OTHER PUBLICATIONS

Elledge et al. (1991) Proc. Natl. Acad. Sci. USA 88: 1731–1735.
Ketchum et al. (1995) Nature 376 (6542): 690–695.
Tang et al. (1995) Mol. Biol. Cell 6: 1231–1240.
Xu et al. (1995) J. Biol. Chem. 270(42): 24761–24768.
Zhou et al. (1995) FEBS Letters 373: 170–176.

*Primary Examiner*—Robert A. Wax
*Assistant Examiner*—Lisa J. Hobbs
*Attorney, Agent, or Firm*—Gale F. Matthews

[57] ABSTRACT

A first aspect of the present invention is the isolation and characterization of invertebrate (i.e. insect and nematode) potassium channel genes. The present invention provides for the isolation of complementary DNA fragments from *Drosophila melanogaster* and *Caenorhabditis elegans* which encode conserved amino acid sequence elements unique to the potassium channel gene family. A yeast expression technology is employed to clone cDNAs from *Drosophila melanogaster* and a hybridization approach is utilized to isolate additional cDNAs from *Caenorhabditis elegans*. Using the yeast expression technology, a single 2463 base pair cDNA fragment designated Dm ORF1 is isolated.

7 Claims, No Drawings

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
( A ) LENGTH: 2441 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 190..2043

( x i ) SEQUENCE DESCRIPTION: SEQ ID NO:1:

```
ACGCGATCGC  CGCGAGTGTA  TATTTTTTTT  TTAGCTCAGT  CTTCAGTGTT  TCGCGATTCT         60

CTTTAAAAGA  AAAAAAAAAT  AATAAGTCAA  AACTACAAAC  CACACAGCGA  AAGGCGAAAG        120

CAACGGTTCC  TGCGAGTGTT  TATTTTTTTT  TTCAACAATT  TTTGATCGTA  GTGCGACAAT        180

CCGTCGAGC  ATG  TCG  CCG  AAT  CGA  TGG  ATC  CTG  CTG  CTC  ATC  TTC  TAC                 228
           Met  Ser  Pro  Asn  Arg  Trp  Ile  Leu  Leu  Leu  Ile  Phe  Tyr
            1              5                             10

ATA  TCC  TAC  CTG  ATG  TTC  GGG  GCG  GCA  ATC  TAT  TAC  CAT  ATT  GAG  CAC           276
Ile  Ser  Tyr  Leu  Met  Phe  Gly  Ala  Ala  Ile  Tyr  Tyr  His  Ile  Glu  His
     15                  20                       25

GGC  GAG  GAG  AAG  ATA  TCG  CGC  GCC  GAA  CAG  CGC  AAG  GCG  CAA  ATT  GCA           324
Gly  Glu  Glu  Lys  Ile  Ser  Arg  Ala  Glu  Gln  Arg  Lys  Ala  Gln  Ile  Ala
 30                       35                  40                          45

ATC  AAC  GAA  TAT  CTG  CTG  GAG  GAG  CTG  GGC  GAC  AAG  AAT  ACG  ACC  ACA           372
Ile  Asn  Glu  Tyr  Leu  Leu  Glu  Glu  Leu  Gly  Asp  Lys  Asn  Thr  Thr  Thr
                        50                       55                  60

CAG  GAT  GAG  ATT  CTT  CAA  CGG  ATC  TCG  GAT  TAC  TGT  GAC  AAA  CCG  GTT           420
Gln  Asp  Glu  Ile  Leu  Gln  Arg  Ile  Ser  Asp  Tyr  Cys  Asp  Lys  Pro  Val
              65                       70                       75

ACA  TTG  CCG  CCG  ACA  TAT  GAT  GAT  ACG  CCC  TAC  ACG  TGG  ACC  TTC  TAC           468
Thr  Leu  Pro  Pro  Thr  Tyr  Asp  Asp  Thr  Pro  Tyr  Thr  Trp  Thr  Phe  Tyr
         80                       85                       90

CAT  GCC  TTC  TTC  TTC  GCC  TTC  ACC  GTT  TGC  TCC  ACG  GTG  GGA  TAT  GGG           516
```

```
His Ala Phe Phe Phe Ala Phe Thr Val Cys Ser Thr Val Gly Tyr Gly
    95              100                 105

AAT ATA TCG CCA ACC ACC TTC GCC GGA CGG ATG ATC ATG ATC GCG TAT     564
Asn Ile Ser Pro Thr Thr Phe Ala Gly Arg Met Ile Met Ile Ala Tyr
110             115                 120                 125

TCG GTG ATT GGC ATC CCC GTC AAT GGT ATC CTC TTT GCC GGC CTC GGC     612
Ser Val Ile Gly Ile Pro Val Asn Gly Ile Leu Phe Ala Gly Leu Gly
                130                 135                 140

GAA TAC TTT GGA CGT ACG TTT GAA GCG ATC TAC AGA CGC TAC AAA AAG     660
Glu Tyr Phe Gly Arg Thr Phe Glu Ala Ile Tyr Arg Arg Tyr Lys Lys
            145                 150                 155

TAC AAG ATG TCC ACG GAT ATG CAC TAT GTC CCG CCG CAG CTG GGA TTG     708
Tyr Lys Met Ser Thr Asp Met His Tyr Val Pro Pro Gln Leu Gly Leu
        160                 165                 170

ATC ACC ACG GTG GTG ATT GCC CTG ATT CCG GGA ATA GCT CTC TTC CTG     756
Ile Thr Thr Val Val Ile Ala Leu Ile Pro Gly Ile Ala Leu Phe Leu
    175                 180                 185

GTG CTG CCC TGC GTG GGT GTT CAC CTA CTT CGA GAA CTG GGC CTA TCT     804
Val Leu Pro Cys Val Gly Val His Leu Leu Arg Glu Leu Gly Leu Ser
190                 195                 200                 205

TCC ATC TCG CTG TAC TAC AGC TAT GTG ACC ACC ACA ACA ATT GGA TTC     852
Ser Ile Ser Leu Tyr Tyr Ser Tyr Val Thr Thr Thr Thr Ile Gly Phe
                210                 215                 220

GGT GAC TAT GTG CCC ACA TTT GGA GCC AAC CAG CCC AAG GAG TTC GGC     900
Gly Asp Tyr Val Pro Thr Phe Gly Ala Asn Gln Pro Lys Glu Phe Gly
            225                 230                 235

GGC TGG TTC GTG GTC TAT CAG ATC TTT GTG ATC GTG TGG TTC ATC TTC     948
Gly Trp Phe Val Val Tyr Gln Ile Phe Val Ile Val Trp Phe Ile Phe
        240                 245                 250

TCG CTG GGA TAT CTT GTG ATG ATC ATG ACA TTT ATC ACT CGG GGC CTC     996
Ser Leu Gly Tyr Leu Val Met Ile Met Thr Phe Ile Thr Arg Gly Leu
    255                 260                 265

CAG AGC AAG AAG CTG GCA TAC CTG GAG CAG CAG TTG TCC TCC AAC CTG     1044
Gln Ser Lys Lys Leu Ala Tyr Leu Glu Gln Gln Leu Ser Ser Asn Leu
270                 275                 280                 285

AAG GCC ACA CAG AAT CGC ATC TGG TCT GGC GTC ACC AAG GAT GTG GGC     1092
Lys Ala Thr Gln Asn Arg Ile Trp Ser Gly Val Thr Lys Asp Val Gly
                290                 295                 300

TAC CTC CGG CGA ATG CTC AAC GAG CTG TAC ATC CTC AAA GTG AAG CCT     1140
Tyr Leu Arg Arg Met Leu Asn Glu Leu Tyr Ile Leu Lys Val Lys Pro
            305                 310                 315

GTG TAC ACC GAT GTA GAT ATC GCC TAC ACA CTG CCA CGT TCC AAT TCG     1188
Val Tyr Thr Asp Val Asp Ile Ala Tyr Thr Leu Pro Arg Ser Asn Ser
        320                 325                 330

TGT CCG GAT CTG AGC ATG TAC CGC GTG GAG CCG GCT CCC ATT CCC AGC     1236
Cys Pro Asp Leu Ser Met Tyr Arg Val Glu Pro Ala Pro Ile Pro Ser
    335                 340                 345

CGG AAG AGG GCA TTC TCC GTG TGC GCC GAC ATG GTT GGC GCC CAA AGG     1284
Arg Lys Arg Ala Phe Ser Val Cys Ala Asp Met Val Gly Ala Gln Arg
350                 355                 360                 365

GAG GCG GGC ATG GTA CAC GCC AAT TCC GAT ACG GAT CTA ACC AAA CTG     1332
Glu Ala Gly Met Val His Ala Asn Ser Asp Thr Asp Leu Thr Lys Leu
                370                 375                 380

GAT CGC GAG AAG ACA TTC GAG ACG GCG GAG GCG TAC CAC CAG ACC ACC     1380
Asp Arg Glu Lys Thr Phe Glu Thr Ala Glu Ala Tyr His Gln Thr Thr
            385                 390                 395

GAT TTG CTG GCC AAG GTG GTC AAC GCA CTG GCC ACG GTG AAG CCA CCG     1428
Asp Leu Leu Ala Lys Val Val Asn Ala Leu Ala Thr Val Lys Pro Pro
        400                 405                 410

CCG GCG GAA CAG GAA GAT GCG GCT CTC TAT GGT GGC TAT CAT GGC TTC     1476
```

|   |   |   |   |   |   |   |   |   |   |   |   |   |   |   |   |   |
|---|---|---|---|---|---|---|---|---|---|---|---|---|---|---|---|---|
| Pro | Ala | Glu | Gln | Glu | Asp | Ala | Ala | Leu | Tyr | Gly | Gly | Tyr | His | Gly | Phe | |
|  | 415 |  |  |  | 420 |  |  |  |  |  | 425 |  |  |  |  | |
| TCC | GAC | TCC | CAG | ATC | CTG | GCC | AGC | GAA | TGG | TCG | TTC | TCG | ACG | GTC | AAC | 1524 |
| Ser | Asp | Ser | Gln | Ile | Leu | Ala | Ser | Glu | Trp | Ser | Phe | Ser | Thr | Val | Asn | |
| 430 |  |  |  |  | 435 |  |  |  |  | 440 |  |  |  |  | 445 | |
| GAG | TTC | ACA | TCA | CCG | CGA | CGT | CCA | AGA | GCA | CGT | GCC | TGC | TCC | GAT | TTC | 1572 |
| Glu | Phe | Thr | Ser | Pro | Arg | Arg | Pro | Arg | Ala | Arg | Ala | Cys | Ser | Asp | Phe | |
|  |  |  |  | 450 |  |  |  |  | 455 |  |  |  |  | 460 |  | |
| AAT | CTG | GAG | GCA | CCT | CGC | TGG | CAG | AGC | GAG | AGG | CCA | CTG | CGT | TCG | AGC | 1620 |
| Asn | Leu | Glu | Ala | Pro | Arg | Trp | Gln | Ser | Glu | Arg | Pro | Leu | Arg | Ser | Ser | |
|  |  |  | 465 |  |  |  |  | 470 |  |  |  |  | 475 |  |  | |
| CAC | AAC | GAA | TGG | ACA | TGG | AGC | GGC | GAC | AAC | CAG | CAG | ATC | CAG | GAG | GCA | 1668 |
| His | Asn | Glu | Trp | Thr | Trp | Ser | Gly | Asp | Asn | Gln | Gln | Ile | Gln | Glu | Ala | |
|  |  | 480 |  |  |  |  | 485 |  |  |  |  | 490 |  |  |  | |
| TTC | AAC | CAG | CGC | TAC | AAG | GGA | CAG | CAG | CGT | GCC | AAC | GGA | GCA | GCC | AAC | 1716 |
| Phe | Asn | Gln | Arg | Tyr | Lys | Gly | Gln | Gln | Arg | Ala | Asn | Gly | Ala | Ala | Asn | |
|  | 495 |  |  |  |  | 500 |  |  |  |  | 505 |  |  |  |  | |
| TCG | ACC | ATG | GTC | CAT | CTG | GAG | CCG | GAT | GCT | TTG | GAG | GAG | CAG | CTG | AGA | 1764 |
| Ser | Thr | Met | Val | His | Leu | Glu | Pro | Asp | Ala | Leu | Glu | Glu | Gln | Leu | Arg | |
| 510 |  |  |  |  | 515 |  |  |  |  | 520 |  |  |  |  | 525 | |
| AAC | AAT | CAC | CGG | GTG | CCG | GTC | GCG | TCA | AGA | AGT | TCT | CCA | TGC | CGG | ATG | 1812 |
| Asn | Asn | His | Arg | Val | Pro | Val | Ala | Ser | Arg | Ser | Ser | Pro | Cys | Arg | Met | |
|  |  |  |  | 530 |  |  |  |  | 535 |  |  |  |  | 540 |  | |
| GTC | TGC | GAC | GTC | TGT | TTC | CCT | TCC | AGA | AGA | AGC | ACC | CCT | CGC | AGG | ATC | 1860 |
| Val | Cys | Asp | Val | Cys | Phe | Pro | Ser | Arg | Arg | Ser | Thr | Pro | Arg | Arg | Ile | |
|  |  |  | 545 |  |  |  |  | 550 |  |  |  |  | 555 |  |  | |
| TGG | AGC | GCA | AGT | TGT | CCG | TGG | TCT | CGG | TAC | CCG | AGG | GTG | TCA | TCT | CGC | 1908 |
| Trp | Ser | Ala | Ser | Cys | Pro | Trp | Ser | Arg | Tyr | Pro | Arg | Val | Ser | Ser | Arg | |
|  |  | 560 |  |  |  |  | 565 |  |  |  |  | 570 |  |  |  | |
| AGG | AAG | CCA | GAT | CCC | CGC | TGG | ACT | ACT | ACA | TCA | ACA | CGG | TCA | CGG | CGG | 1956 |
| Arg | Lys | Pro | Asp | Pro | Arg | Trp | Thr | Thr | Thr | Ser | Thr | Arg | Ser | Arg | Arg | |
| 575 |  |  |  |  | 580 |  |  |  |  | 585 |  |  |  |  |  | |
| CCT | CCA | GTC | AAT | CCT | ATT | TGC | GCA | ACG | GAC | GCG | GTC | CGC | CAC | CGC | CCT | 2004 |
| Pro | Pro | Val | Asn | Pro | Ile | Cys | Ala | Thr | Asp | Ala | Val | Arg | His | Arg | Pro | |
| 590 |  |  |  |  | 595 |  |  |  |  | 600 |  |  |  |  | 605 | |
| TCG | AAT | CGA | ATG | GCA | GCT | TGG | CCA | GCG | GCG | GCG | GCG | GGC | TAACGAACAT |  |  | 2053 |
| Ser | Asn | Arg | Met | Ala | Ala | Trp | Pro | Ala | Ala | Ala | Ala | Gly |  |  |  | |
|  |  |  | 610 |  |  |  |  |  | 615 |  |  |  |  |  |  | |

```
GGGCTTCCAG ATGGAGGATG GAGCAACCCC GCCATCGGCA TTGGGCGGTG GAGCCTATCA    2113
ACGCAAGGCG GCTGCTGGCA AGCGCCGACG CGAGAGCATC TACACCCAGA ATCAAGCCCC    2173
ATCCGCTCGC CGGGGCAGCA TGTATCCGCC GACCGCGCAC GCCTTGGCCC AGATGCAGAT    2233
GCGACGCGGC AGCTTGGCAA CCAGTGGCTC TGGATCGGCG GCCATGGCGG CAGTGGCCGC    2293
GCGTCGTGGC AGCCTCTTCC CAGCTACAGC ATCGGCATCA TCGCTGACCT CTGCTCCGCG    2353
CCGAAGCAGC ATATTCTCGG TTACCTCCGA AAAGGATATG AATGTGCTGG AGCAGACGAC    2413
CATTGCGGAT CTGATTCGTG CGCTCGAG                                       2441
```

( 2 ) INFORMATION FOR SEQ ID NO:2:

( i ) SEQUENCE CHARACTERISTICS:
        ( A ) LENGTH: 618 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

|   |   |   |   |   |   |   |   |   |   |   |   |   |   |   |
|---|---|---|---|---|---|---|---|---|---|---|---|---|---|---|
| Met | Ser | Pro | Asn | Arg | Trp | Ile | Leu | Leu | Leu | Ile | Phe | Tyr | Ile | Ser | Tyr |
| 1 |  |  |  | 5 |  |  |  |  | 10 |  |  |  |  | 15 |

```
Leu  Met  Phe  Gly  Ala  Ala  Ile  Tyr  Tyr  His  Ile  Glu  His  Gly  Glu  Glu
              20                  25                      30

Lys  Ile  Ser  Arg  Ala  Glu  Gln  Arg  Lys  Ala  Gln  Ile  Ala  Ile  Asn  Glu
                   35                  40                      45

Tyr  Leu  Leu  Glu  Glu  Leu  Gly  Asp  Lys  Asn  Thr  Thr  Thr  Gln  Asp  Glu
         50                      55                      60

Ile  Leu  Gln  Arg  Ile  Ser  Asp  Tyr  Cys  Asp  Lys  Pro  Val  Thr  Leu  Pro
65                           70                      75                      80

Pro  Thr  Tyr  Asp  Asp  Thr  Pro  Tyr  Thr  Trp  Thr  Phe  Tyr  His  Ala  Phe
                        85                      90                      95

Phe  Phe  Ala  Phe  Thr  Val  Cys  Ser  Thr  Val  Gly  Tyr  Gly  Asn  Ile  Ser
              100                      105                     110

Pro  Thr  Thr  Phe  Ala  Gly  Arg  Met  Ile  Met  Ile  Ala  Tyr  Ser  Val  Ile
         115                      120                     125

Gly  Ile  Pro  Val  Asn  Gly  Ile  Leu  Phe  Ala  Gly  Leu  Gly  Glu  Tyr  Phe
     130                      135                     140

Gly  Arg  Thr  Phe  Glu  Ala  Ile  Tyr  Arg  Arg  Tyr  Lys  Lys  Tyr  Lys  Met
145                      150                     155                     160

Ser  Thr  Asp  Met  His  Tyr  Val  Pro  Pro  Gln  Leu  Gly  Leu  Ile  Thr  Thr
                   165                      170                     175

Val  Val  Ile  Ala  Leu  Ile  Pro  Gly  Ile  Ala  Leu  Phe  Leu  Val  Leu  Pro
              180                      185                     190

Cys  Val  Gly  Val  His  Leu  Leu  Arg  Glu  Leu  Gly  Leu  Ser  Ser  Ile  Ser
         195                      200                     205

Leu  Tyr  Tyr  Ser  Tyr  Val  Thr  Thr  Thr  Ile  Gly  Phe  Gly  Asp  Tyr
     210                      215                     220

Val  Pro  Thr  Phe  Gly  Ala  Asn  Gln  Pro  Lys  Glu  Phe  Gly  Gly  Trp  Phe
225                      230                     235                     240

Val  Val  Tyr  Gln  Ile  Phe  Val  Ile  Val  Trp  Phe  Ile  Phe  Ser  Leu  Gly
                   245                      250                     255

Tyr  Leu  Val  Met  Ile  Met  Thr  Phe  Ile  Thr  Arg  Gly  Leu  Gln  Ser  Lys
              260                      265                     270

Lys  Leu  Ala  Tyr  Leu  Glu  Gln  Gln  Leu  Ser  Ser  Asn  Leu  Lys  Ala  Thr
         275                      280                     285

Gln  Asn  Arg  Ile  Trp  Ser  Gly  Val  Thr  Lys  Asp  Val  Gly  Tyr  Leu  Arg
290                      295                     300

Arg  Met  Leu  Asn  Glu  Leu  Tyr  Ile  Leu  Lys  Val  Lys  Pro  Val  Tyr  Thr
305                      310                     315                     320

Asp  Val  Asp  Ile  Ala  Tyr  Thr  Leu  Pro  Arg  Ser  Asn  Ser  Cys  Pro  Asp
                   325                      330                     335

Leu  Ser  Met  Tyr  Arg  Val  Glu  Pro  Ala  Pro  Ile  Pro  Ser  Arg  Lys  Arg
              340                      345                     350

Ala  Phe  Ser  Val  Cys  Ala  Asp  Met  Val  Gly  Ala  Gln  Arg  Glu  Ala  Gly
         355                      360                     365

Met  Val  His  Ala  Asn  Ser  Asp  Thr  Asp  Leu  Thr  Lys  Leu  Asp  Arg  Glu
370                      375                     380

Lys  Thr  Phe  Glu  Thr  Ala  Glu  Ala  Tyr  His  Gln  Thr  Thr  Asp  Leu  Leu
385                      390                     395                     400

Ala  Lys  Val  Val  Asn  Ala  Leu  Ala  Thr  Val  Lys  Pro  Pro  Pro  Ala  Glu
                   405                      410                     415

Gln  Glu  Asp  Ala  Ala  Leu  Tyr  Gly  Gly  Tyr  His  Gly  Phe  Ser  Asp  Ser
              420                      425                     430

Gln  Ile  Leu  Ala  Ser  Glu  Trp  Ser  Phe  Ser  Thr  Val  Asn  Glu  Phe  Thr
         435                      440                     445
```

```
Ser  Pro  Arg  Arg  Pro  Arg  Ala  Arg  Ala  Cys  Ser  Asp  Phe  Asn  Leu  Glu
     450                 455                 460

Ala  Pro  Arg  Trp  Gln  Ser  Glu  Arg  Pro  Leu  Arg  Ser  Ser  His  Asn  Glu
465                      470                 475                      480

Trp  Thr  Trp  Ser  Gly  Asp  Asn  Gln  Gln  Ile  Gln  Glu  Ala  Phe  Asn  Gln
               485                 490                           495

Arg  Tyr  Lys  Gly  Gln  Gln  Arg  Ala  Asn  Gly  Ala  Ala  Asn  Ser  Thr  Met
               500                 505                      510

Val  His  Leu  Glu  Pro  Asp  Ala  Leu  Glu  Glu  Gln  Leu  Arg  Asn  Asn  His
          515                 520                      525

Arg  Val  Pro  Val  Ala  Ser  Arg  Ser  Ser  Pro  Cys  Arg  Met  Val  Cys  Asp
     530                 535                      540

Val  Cys  Phe  Pro  Ser  Arg  Arg  Ser  Thr  Pro  Arg  Arg  Ile  Trp  Ser  Ala
545                      550                      555                      560

Ser  Cys  Pro  Trp  Ser  Arg  Tyr  Pro  Arg  Val  Ser  Ser  Arg  Arg  Lys  Pro
               565                      570                           575

Asp  Pro  Arg  Trp  Thr  Thr  Thr  Ser  Thr  Arg  Ser  Arg  Arg  Pro  Pro  Val
               580                      585                      590

Asn  Pro  Ile  Cys  Ala  Thr  Asp  Ala  Val  Arg  His  Arg  Pro  Ser  Asn  Arg
          595                 600                      605

Met  Ala  Ala  Trp  Pro  Ala  Ala  Ala  Gly
     610                 615
```

( 2 ) INFORMATION FOR SEQ ID NO:3:

( i ) SEQUENCE CHARACTERISTICS:
        ( A ) LENGTH: 1011 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: CDS
        ( B ) LOCATION: 1..1008

( x i ) SEQUENCE DESCRIPTION: SEQ ID NO:3:

```
ATG  TCC  GAT  CAG  CTG  TTT  GTC  GCA  TTT  GAG  AAG  TAT  TTC  TTG  ACG  AGT     48
Met  Ser  Asp  Gln  Leu  Phe  Val  Ala  Phe  Glu  Lys  Tyr  Phe  Leu  Thr  Ser
  1                 5                   10                      15

AAC  GAG  GTC  AAG  AAG  AAT  GCA  GCA  ACG  GAG  ACA  TGG  ACA  TTT  TCA  TCG     96
Asn  Glu  Val  Lys  Lys  Asn  Ala  Ala  Thr  Glu  Thr  Trp  Thr  Phe  Ser  Ser
               20                  25                      30

TCC  ATT  TTC  TTT  GCC  GTA  ACC  GTC  GTC  ACT  ACC  ATC  GGA  TAC  GGT  AAT    144
Ser  Ile  Phe  Phe  Ala  Val  Thr  Val  Val  Thr  Thr  Ile  Gly  Tyr  Gly  Asn
          35                       40                      45

CCA  GTT  CCA  GTG  ACA  AAC  ATT  GGA  CGG  ATA  TGG  TGT  ATA  TTG  TTC  TCC    192
Pro  Val  Pro  Val  Thr  Asn  Ile  Gly  Arg  Ile  Trp  Cys  Ile  Leu  Phe  Ser
     50                  55                       60

TTG  CTT  GGA  ATA  CCT  CTA  ACA  CTG  GTT  ACC  ATC  GCT  GAC  TTG  GCA  GGT    240
Leu  Leu  Gly  Ile  Pro  Leu  Thr  Leu  Val  Thr  Ile  Ala  Asp  Leu  Ala  Gly
 65                      70                       75                      80

AAA  TTC  CTA  TCT  GAA  CAT  CTT  GTT  TGG  TTG  TAT  GGA  AAC  TAT  TTG  AAA    288
Lys  Phe  Leu  Ser  Glu  His  Leu  Val  Trp  Leu  Tyr  Gly  Asn  Tyr  Leu  Lys
                    85                  90                           95

TTA  AAA  TAT  CTC  ATA  TTG  TCA  CGA  CAT  CGA  AAA  GAA  CGG  AGA  GAG  CAC    336
Leu  Lys  Tyr  Leu  Ile  Leu  Ser  Arg  His  Arg  Lys  Glu  Arg  Arg  Glu  His
                    100                 105                      110

GTT  TGT  GAG  CAC  TGT  CAC  AGT  CAT  GGA  ATG  GGG  CAT  GAT  ATG  AAT  ATC    384
```

|   |   |   |   |   |   |   |   |   |   |   |   |   |   |   |   |
|---|---|---|---|---|---|---|---|---|---|---|---|---|---|---|---|
| Val | Cys | Glu<br>115 | His | Cys | His | Ser | His<br>120 | Gly | Met | Gly | His<br>125 | Asp | Met | Asn | Ile |

```
GAG GAG AAA AGA ATT CCT GCA TTC CTG GTA TTA GCT ATT CTG ATA GTA     432
Glu Glu Lys Arg Ile Pro Ala Phe Leu Val Leu Ala Ile Leu Ile Val
    130                 135                 140

TAT ACA GCG TTT GGC GGT GTC CTA ATG TCA AAA TTA GAG CCG TGG TCT     480
Tyr Thr Ala Phe Gly Gly Val Leu Met Ser Lys Leu Glu Pro Trp Ser
145                 150                 155                 160

TTC TTC ACT TCA TTC TAC TGG TCC TTC ATT ACA ATG ACT ACT GTC GGG     528
Phe Phe Thr Ser Phe Tyr Trp Ser Phe Ile Thr Met Thr Thr Val Gly
                165                 170                 175

TTT GGC GAC TTG ATG CCC AGA AGG GAC GGA TAC ATG TAT ATA ATA TTG     576
Phe Gly Asp Leu Met Pro Arg Arg Asp Gly Tyr Met Tyr Ile Ile Leu
            180                 185                 190

CTC TAT ATC ATT TTA GGT AAA TTT TCA ATG AAA AAA AAA CAA AAA TTC     624
Leu Tyr Ile Ile Leu Gly Lys Phe Ser Met Lys Lys Lys Gln Lys Phe
        195                 200                 205

AAA ATA TTT TTA GGT CTT GCA ATA ACT ACA ATG TGC ATT GAT TTG GTA     672
Lys Ile Phe Leu Gly Leu Ala Ile Thr Thr Met Cys Ile Asp Leu Val
    210                 215                 220

GGA GTA CAG TAT ATT CGA AAG ATT CAT TAT TTC GGA AGA AAA ATT CAA     720
Gly Val Gln Tyr Ile Arg Lys Ile His Tyr Phe Gly Arg Lys Ile Gln
225                 230                 235                 240

GAC GCT AGA TCT GCA TTG GCG GTT GTA GGA GGA AAG GTA GTC CTT GTA     768
Asp Ala Arg Ser Ala Leu Ala Val Val Gly Gly Lys Val Val Leu Val
                245                 250                 255

TCA GAA CTC TAC GCA AAT TTA ATG CAA AAG CGA GCT CGT AAC ATG TCC     816
Ser Glu Leu Tyr Ala Asn Leu Met Gln Lys Arg Ala Arg Asn Met Ser
            260                 265                 270

CGA GAA GCT TTT ATA GTG GAG AAT CTC TAT GTT TCC AAA CAC ATC ATA     864
Arg Glu Ala Phe Ile Val Glu Asn Leu Tyr Val Ser Lys His Ile Ile
        275                 280                 285

CCA TTC ATA CCA ACT GAT ATC CGA TGT ATT CGA TAT ATT GAT CAA ACT     912
Pro Phe Ile Pro Thr Asp Ile Arg Cys Ile Arg Tyr Ile Asp Gln Thr
    290                 295                 300

GCC GAT GCT GCT ACC ATT TCC ACG TCA TCG TCT GCA ATT GAT ATG CAA     960
Ala Asp Ala Ala Thr Ile Ser Thr Ser Ser Ser Ala Ile Asp Met Gln
305                 310                 315                 320

AGT TGT AGA TTT TGT CAT TCA AGA TAT TCT CTC AAT CGT GCA TTC AAA    1008
Ser Cys Arg Phe Cys His Ser Arg Tyr Ser Leu Asn Arg Ala Phe Lys
                325                 330                 335

TAG                                                                1011
```

( 2 ) INFORMATION FOR SEQ ID NO:4:

( i ) SEQUENCE CHARACTERISTICS:
        ( A ) LENGTH: 336 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

```
Met Ser Asp Gln Leu Phe Val Ala Phe Glu Lys Tyr Phe Leu Thr Ser
 1               5                  10                  15

Asn Glu Val Lys Lys Asn Ala Ala Thr Glu Thr Trp Thr Phe Ser Ser
                20                  25                  30

Ser Ile Phe Phe Ala Val Thr Val Val Thr Thr Ile Gly Tyr Gly Asn
                35                  40                  45

Pro Val Pro Val Thr Asn Ile Gly Arg Ile Trp Cys Ile Leu Phe Ser
    50                  55                  60
```

| | | | | | | | | | | | | | | |
|---|---|---|---|---|---|---|---|---|---|---|---|---|---|---|
| Leu 65 | Leu | Gly | Ile | Pro | Leu 70 | Thr | Leu | Val | Ile 75 | Ala | Asp | Leu | Ala | Gly 80 |
| Lys | Phe | Leu | Ser | Glu 85 | His | Leu | Val | Trp | Leu 90 | Tyr | Gly | Asn | Tyr | Leu Lys 95 |
| Leu | Lys | Tyr | Leu 100 | Ile | Leu | Ser | Arg | His 105 | Arg | Lys | Glu | Arg 110 | Glu | His |
| Val | Cys | Glu 115 | His | Cys | His | Ser | His 120 | Gly | Met | Gly | His | Asp 125 | Met | Asn Ile |
| Glu | Glu 130 | Lys | Arg | Ile | Pro | Ala 135 | Phe | Leu | Val | Leu | Ala 140 | Ile | Leu | Ile Val |
| Tyr 145 | Thr | Ala | Phe | Gly | Gly 150 | Val | Leu | Met | Ser | Lys 155 | Leu | Glu | Pro | Trp Ser 160 |
| Phe | Phe | Thr | Ser | Phe 165 | Tyr | Trp | Ser | Phe | Ile 170 | Thr | Met | Thr | Thr 175 | Val Gly |
| Phe | Gly | Asp | Leu 180 | Met | Pro | Arg | Arg | Asp 185 | Gly | Tyr | Met | Tyr | Ile 190 | Ile Leu |
| Leu | Tyr | Ile 195 | Ile | Leu | Gly | Lys | Phe 200 | Ser | Met | Lys | Lys | Lys 205 | Gln | Lys Phe |
| Lys | Ile 210 | Phe | Leu | Gly | Leu | Ala 215 | Ile | Thr | Thr | Met | Cys 220 | Ile | Asp | Leu Val |
| Gly 225 | Val | Gln | Tyr | Ile | Arg 230 | Lys | Ile | His | Tyr | Phe 235 | Gly | Arg | Lys | Ile Gln 240 |
| Asp | Ala | Arg | Ser | Ala 245 | Leu | Ala | Val | Val | Gly 250 | Gly | Lys | Val | Val | Leu Val 255 |
| Ser | Glu | Leu | Tyr 260 | Ala | Asn | Leu | Met | Gln 265 | Lys | Arg | Ala | Arg | Asn 270 | Met Ser |
| Arg | Glu | Ala 275 | Phe | Ile | Val | Glu | Asn 280 | Leu | Tyr | Val | Ser | Lys 285 | His | Ile Ile |
| Pro | Phe 290 | Ile | Pro | Thr | Asp | Ile 295 | Arg | Cys | Ile | Arg | Tyr 300 | Ile | Asp | Gln Thr |
| Ala 305 | Asp | Ala | Ala | Thr | Ile 310 | Ser | Thr | Ser | Ser | Ser 315 | Ala | Ile | Asp | Met Gln 320 |
| Ser | Cys | Arg | Phe | Cys 325 | His | Ser | Arg | Tyr | Ser 330 | Leu | Asn | Arg | Ala | Phe Lys 335 |

GENES ENCODING A NOVEL FAMILY OF POTASSIUM CHANNELS

FIELD OF INVENTION

This invention relates generally to the potassium channel gene family. More particularly, the present invention relates to the cloning and characterization of potassium channel genes from Drosophila melanogaster and Caenorhabditis elegans.

BACKGROUND OF THE INVENTION

Synthetic organic insecticides are primarily nerve poisons acting on the cholinergic system (organophosphorus compounds and methylcarbamates), the voltage-gated sodium channel (pyrethroids and DDT), and the GABA-gated chloride channel (cyclodienes and other polychlorocycloalkanes). Potassium channels comprise a large and diverse group of integral membrane proteins that determine the level of excitability and repolarization properties of neurons and muscle fibers [B. Hille, *Ionic Channels of Excitable Membranes,* Sinauer, Sunderland, Mass. (1984)]. The multiple essential functions encoded by the potassium channels make them excellent targets for new pesticides and animal and human therapeutics. Potassium channel diversity in the fruitfly Drosophila melanogaster results from an extended gene family coding for homologous proteins. Six genes encoding potassium channels have been cloned from Drosophila melanogaster which account for a large part of the diversity of potassium currents observed in insect nervous tissue [A. Wei, M. Covarrubias, A. Butler, K. Baker, M. Pak, L. Salkoff, *Science* 248, 599–603 (1990), N. S. Atkinson, G. A. Robertson, B. Ganetzky, *Science* 253, 551–555, (1991), J. Warmke, R. Drysdale, B. Ganetzky, *Science* 252, 1560–1564 (1991), A. Bruggemann, L. A. Pardo, W. Stuhmer, O. Pongs, *Nature* 365, 445–448 (1993)]. Shaker and Shal encode voltage-gated potassium channels with rapid current activation and inactivating properties. Shab and Shaw encode delayed rectifier channels, with slow inactivating (Shab) and non-inactivating (Shaw) properties. Slo encodes a calcium-activated potassium channel and eag encodes a voltage-gated channel permeable to both potassium and calcium which is modulated by cyclic AMP.

Modulation of cardiac action potential by compounds that effect the behavior of potassium channels may be a useful treatment for serious heart conditions. In this regard, each of the potassium channels cloned from insects have corresponding versions in mammalian species, including, specifically, a delayed rectifier potassium channel homolog, RAK, cloned from rat cardiac tissue [M. Paulmichl, P. Nasmith, R. Hellmiss, K. Reed, W. A. Boyle, J. M. Nerbonne, E. G. Peralta, D. E. Clapham, *Proc. Natl. Acad. Sci USA* 88, 7892–7895 (1991)]. Thus, the RAK channel represents an important target of new drugs for the control of heart failure. The delayed rectifier potassium current in heart cells regulates the duration of the plateau of the cardiac action potential by countering the depolarizing, inward calcium current. Delayed rectifier potassium currents characteristically are activated upon depolarization from rest, display a sigmoidal or delayed onset, and have a nonlinear, or rectifying, current-voltage relation. Several types of delayed potassium conductances have been identified in cardiac cells based on measured single-channel conductances. Heart rate and contractility are regulated by second messenger modification of delayed rectifier potassium conductances, and species differences in the shape of the plateau may be influenced by the type and level of channel expression.

On the basis of predicted membrane spanning topology, potassium channels may be subdivided into two distinct classes: voltage-gated, calcium-activated, and cyclic nucleotide-gated potassium channels that are composed of six membrane spanning domains (S1–S6) and a single pore forming domain (H5), and inward rectifying potassium channels that pass through the membrane twice and also contain a single pore forming region [Y. Kubo, E. Reuveny, P. A. Slesinger, Y. N. Jan, L. Y. Jan *Nature* 364, 802–806 (1993); Y. Kubo, T. J. Baldwin, Y. N. Jan, L. Y. Jan *Nature* 362, 127–133 (1993)]. Here, we report the cloning and functional expression in yeast of a novel Drosophila melanogaster potassium channel. Further, we identify a Caenorhabditis elegans homolog that constitutes the second member of a new family of potassium channels exhibiting a topological configuration unique among the known classes of potassium channels.

The yeast *Saccharomyces cerevisiae* is utilized as a model eukaryotic organism for the purpose of studying potassium transport mechanisms. Due to the ease with which one can manipulate the genetic constitution of the yeast *Saccharomyces cerevisiae,* researchers have developed a detailed understanding of many complex biological pathways, including potassium transport. In yeast, high affinity potassium uptake is performed by the product of the TRK1 gene [R. F. Gaber, C. A. Styles, G. R. Fink *Mol. Cell. Biol.* 8, 2848–2859 (1988)]. Mutant yeast strains lacking trk1 function are incapable of growing in medium lacking high concentrations of potassium. Since potassium transport mechanisms are present in organisms as divergent as yeast and man, one could predict that expression of heterologous potassium channels in mutant cells might replace trk1 function, and support growth on medium containing low potassium concentration. In this regard, plant potassium channels were shown to function in yeast and represent important targets for new herbicides [J. A. Anderson, S. S. Huprikar, L. V. Kochian, W. J. Lucas, R. F. Gaber, *Proc. Natl. Acad. Sci USA* 89, 3736–3740 (1992); H. Sentenac, N. Bonnaud, M. Minet, F. Lacroute, J.-M. Salmon, F. Gaynard, C. Grignon, *Science* 256, 663–665 (1992); D. P. Schachtman and J. I. Schroeder, *Nature* 370, 655–658]. Thus, we have employed this yeast expression system for cloning and expression of potassium channels from heterologous species, making it useful for discovery of new pesticides, and animal and human therapeutics. Discovery of such compounds will necessarily require screening assays of high specificity and throughput. For example, new pesticides directed at potassium channels require high selectivity for insect channels and low activity against non-insect species. Screening assays utilizing yeast strains genetically modified to accommodate functional expression of heterologous potassium channels offer significant advantages in this area.

SUMMARY OF THE INVENTION

A first aspect of the present invention is the isolation and characterization of invertebrate (i.e. insect and nematode) potassium channel genes. The present invention provides for the isolation of complementary DNA fragments from Drosophila melanogaster and Caenorhabditis elegans which encode conserved amino acid sequence elements unique to the potassium channel gene family. A yeast expression technology is employed to clone cDNAs from Drosophila melanogaster and a hybridization approach is utilized to isolate additional cDNAs from Caenorhabditis elegans.

Using the yeast expression technology, a single 2463 base pair cDNA fragment designated Dm ORF1 is isolated by complementation of the potassium-dependent phenotype of *Saccharomyces cerevisiae* strain CY162 (trk1Δ) on medium containing low potassium concentration [J. A. Anderson, S. S. Huprikar, L. V. Kochian, W. J. Lucas, R. F. Gaber, *Proc. Natl. Acad. Sci USA* 89, 3736–3740 (1992)]. Dm ORF1 contains a single long open reading frame encoding a protein of 618 amino acids that exhibits substantial amino acid identity to the pore-forming regions of other potassium channels. The DmORF1 contains structural features that distinguish it from other classes of potassium channels, including four hydrophobic domains capable of forming transmembrane helices (M1–M4) and two putative pore forming H5 domains found between transmembrane helices M1 and M2, and M3 and M4. Each pore forming H5 domain contains the Y/F-G dipeptide motif required for potassium selectivity [L. Heginbotham, T. Abramson, R. MacKinnon, *Science* 258, 1152–1155, (1992)].

A search of the GENBANK database for DNA and protein sequences similar to DmORF1 reveals several cloned potassium channel sequences including a putative protein coding DNA sequence, F22b7.7, reported in the *Caenorhabditis elegans* genome sequencing project [R. Wilson, R. Ainscough, K. Anderson, et al. *Nature* 368, 32–38 (1994)]. The DNA sequence contains a single long open reading frame sufficient to encode a protein of 336 amino acids (predicted MW 38.5 kDa) with substantial homology to known potassium channel sequences.

Using the hybridization approach, a cDNA sequence designated CeORF1 is isolated by probing a *Caenorhabditis elegans* cDNA library with oligonucleotides designed using F22b7.7 DNA sequences [T. N. Davis and J. Thorner *Meth. Enzymol.* 139, 246–262 (1987)]. CeORF1 contains a single long open reading frame encoding a protein that exhibits substantial amino acid identity to pore-forming regions of other potassium channels. CeORF1 contains structural features similar to DmORF1, including two putative pore forming H5 domains. Each pore forming H5 domain contains the Y/F-G dipeptide motif required for potassium selectivity [L. Heginbotham, T. Abramson, R. MacKinnon, *Science* 258, 1152–1155, (1992)]. These features form the basis of the designation of a new sub-family of potassium channels composed of DmORF1 and CeORF1.

A second aspect of the present invention is a transformed yeast cell containing a heterologous DNA sequence which codes for a rat cardiac delayed rectifier potassium channel, RAK, cloned into a suitable expression vector. RAK is capable of complementing the potassium-dependent phenotype of *Saccharomyces cerevisiae* strain CY162 on medium containing low potassium concentration. A third aspect of the present invention is a method of assaying compounds to determine effects on cell growth. Yeast cells of the kind described above are cultured in appropriate growth medium to cause expression of heterologous proteins, embedded in agar growth medium, and exposed to chemical compounds applied to the surface of the agar plates. Effects on the growth of embedded cells are found around compounds that have effects on the heterologous potassium channel.

DETAILED DESCRIPTION OF THE INVENTION

Nucleotide bases are abbreviated herein as follows:
Ade; A-AdenineG-GuanineUra; U-Uracil
C-CytosineT-Thymine Amino acid residues are abbreviated herein to either three letters or a single letter as follows:
Ala; A-AlanineLeu; L-Leucine
Arg; R-ArginineLys; K-Lysine
Asn; N-AsparagineMet; M-Methionine
Asp; D-Aspartic acidPhe; F-Phenylalanine
Cys; C-CysteinePro; P-Proline
Gln; Q-GlutamineSer; S-Serine
Glu; E-Glutamic acidThr; T-Threonine
Gly; G-GlycineTrp; W-Tryptophan
His; H-HistidineTyr; Y-Tyrosine
Ile; I-IsoleucineVal; V-Valine The term "mammalian" as used herein refers to any mammalian species (e.g., human, mouse, rat, and monkey).

The term "heterologous" is used herein with respect to yeast, and hence refers to DNA sequences, proteins, and other materials originating from organisms other than yeast (e.g., mammalian, arian, amphibian, insect, plant), or combinations thereof not naturally found in yeast.

The terms "upstream" and "downstream" are used herein to refer to the direction of transcription and translation, with a sequence being transcribed or translated prior to another sequence being referred to as "upstream" of the latter.

Any potassium channels may be employed in practicing the present invention. Examples of such channels include, but are not limited to, voltage-gated channels, calcium activated channels, cyclic nucleotide gated channels, and inward rectifier channels. The term channel as used herein is intended to encompass subtypes of the named channels from any metazoa species, and mutants and homologs thereof, along with the DNA sequences encoding the same. Heterologous DNA sequences are expressed in a host by means of an expression vector. An expression vector is a replicable DNA construct in which a DNA sequence encoding the heterologous DNA sequence is operably linked to suitable control sequences capable of affecting the expression of a protein or protein subunit coded for by the heterologous DNA sequence in the intended host. Generally, control sequences include a transcriptional promoter, an optional operator sequence to control transcription, a sequence encoding suitable mRNA ribosomal binding sites, and (optionally) sequences which control the termination of transcription and translation. Vectors useful for practicing the present invention include plasmids, viruses (including bacteriophage), and integratable DNA fragments (i.e., fragments integratable into the host genome by genetic recombination). The vector may replicate and function independently of the host genome, as in the case of a plasmid, or may integrate into the genome itself, as in the case of an integratable DNA fragment. Suitable vectors will contain replicon and control sequences which are derived from species compatible with the intended expression host. For example, a promoter operable in a host cell is one which binds the RNA polymerase of that cell, and a ribosomal binding site operable in a host cell is one which binds the endogenous ribosomes of that cell.

DNA regions are operably associated when they are functionally related to each other. For example, a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Transformed host cells of the present invention are cells which have been transformed or transfected with the vectors constructed using recombinant DNA techniques and express the protein or protein subunit coded for by the heterologous DNA sequences. A variety of yeast cultures, and suitable expression vectors for transforming yeast cells, are known.

See e.g., U.S. Pat. No. 4,745,057; U.S. Pat. No. 4,797,359; U.S. Pat. No. 4,615,974; U.S. Pat. No. 4,880,734; U.S. Pat. No. 4,711,844; and U.S. Pat. No. 4,865,989. *Saccharomyces cerevisiae* is the most commonly used among the yeasts, although a number of other yeast species are commonly available. See. e.g., U.S. Pat. No. 4,806,472 (*Kluveromyces lactis* and expression vectors therefore); 4,855,231 (*Pichia pastoris* and expression vectors therefore). A heterologous potassium channel may permit a yeast strain unable to grow in medium containing low potassium concentration to survive [CY162, for example, see J. A Anderson, S. S. Huprikar, L. V. Kochian, W. J. Lucas, R. F. Gaber, *Proc. Natl. Acad. Sci USA* 89, 3736–3740 (1992)]. Yeast vectors may contain an origin of replication from the endogenous 2 micron (2 m) yeast plasmid or an autonomously replicating sequence (ARS) which confer on the plasmid the ability to replicate at high copy number in the yeast cell, centromeric (CEN) sequences which limit the ability of the plasmid to replicate at only low copy number in the yeast cell, a promoter, DNA encoding the heterologous DNA sequences, sequences for poly-adenylation and transcription termination, and a selectable marker gene. An exemplary plasmid is YRp7, (Stinchcomb et al., (1979) *Nature* 282, 39; Kingsman et al., (1979) *Gene* 7, 141; Tschemper et al., (1980) *Gene* 10, 157]. This plasmid contains the TRP1 gene, which provides a selectable marker for a mutant strain of yeast lacking the ability to grow in the absence of tryptophan, for example ATCC No. 44076. The presence of the trp1 lesion in the yeast host cell genome then provides an effective environment for detecting transformation by growth in the absence of tryptophan.

Suitable promoting sequences in yeast vectors include the promoters for metallothionein (YEp52), 3-phosphoglycerate kinase [pPGKH, Hitzeman et al., (1980) *J. Biol. Chem.* 255, 2073] or other glycolytic enzymes [pYSK153, Hess et al., (1968) *J. Adv. Enzyme Reg.* 7, 149]; and Holland et al., (1978) *Biochemistry* 17, 4900], such as enolase, glyceraldehyde-3-phosphate dehydrogenase, hexokinase, pyruvate decarboxylase, phospho-fructokinase, glucose- 6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657. Other promoters, which have the additional advantage of transcription controlled by growth conditions, are the promoter regions for alcohol dehydrogenase 2 (pAD4M), isocytochrome C, acid phosphates, degradative enzymes associated with nitrogen metabolism, and the aforementioned metallothionein and glyceraldehyde-3-phosphate dehydrogenase, as well as enzymes responsible for maltose and galactose (pYES2) utilization. Finally, in constructing suitable expression plasmids, the termination sequences associated with these genes may also be ligated into the expression vector 3' of the heterologous coding sequences to provide polyadenylation and termination of the mRNA. A yeast expression system is described here wherein yeast cells bearing heterologous potassium channels for continued growth. As noted above, transformed host cells of the present invention express the proteins or proteins subunit coded for by the heterologous DNA sequences. When expressed, the potassium channel is located in the host cell membrane (i.e., physically positioned therein in proper orientation for both the stereoselective binding of ligands and passage of potassium ions). The following Examples are provided to further illustrate various aspects of the present invention. They are not to be construed as limiting the invention.

EXAMPLE 1

Recombinant Expression Library Screening

*Saccharomyces cerevisiae* strain CY162 is described in Anderson, J. A. et al. (1992) *Proc. Natl. Adad. Sci. USA* 89, 3736–3740]. Growth of bacterial strains and plasmid manipulations are performed by standard methods (Maniatis T., Molecular Cloning. Cold Spring Harbor Laboratory Press, 1982). Media conditions for growth of yeast, isolation of plasmid DNA from yeast, and DNA-mediated transformation of yeast strains are as described (Rose M. D., Methods in yeast genetics, Cold Spring Harbor Laboratory Press, 1990). A multifunctional expression library constructed in pYES2 and containing cDNA made from 3rd instar male *Drosophila melanogaster* mRNA is used as described [S. J. Elledge, J. T. Mulligan, S. W. Ramer, M. Sportswood, R. W. Davis *Proc. Natl. Acad. Sci USA* 88, 1731–1735 (1991)]. A multifunctional expression library constructed in pYES2 and containing cDNA made from mRNA obtained from all life stages of *Caenorhabditis elegans* is custom-made by Invitrogen Corporation.

Isolation of Expression Plasmids Encoding Heterologous Potassium Channels

CY162 cells are transformed with plasmid DNA from each library to give $3 \times 10^6$ transformants from each library on SCD-ura (synthetic complete dextrose (2 %) medium containing all necessary nutritional supplements except uracil) containing 0.1M KCl agar medium. Transformants are replica-plated to SCG-ura (synthetic complete galactose (2%) medium containing all necessary nutritional supplements except uracil) agar medium. Colonies that grow on this selective agar medium are transferred to SCG-ura agar medium to obtain single colonies clones and while reassaying suppression of the potassium-dependent phenotype. Plasmid DNA is isolated from surviving colonies and used to transform CY162. Six individual transformant strains containing one plasmid, pDmORF1, that confers the potassium independent phenotype are cultured on SCD-ura and SCG-ura medium along with CY162 strains bearing pKAT1, which encodes a plant inward rectifier potassium channel that supports the growth of CY162 on selective medium. The plasmid bearing strains exhibit potassium-independent growth on both dextrose and galactose containing medium. Growth on dextrose is likely due to basal level of transcription leading to sufficient potassium channel expression to support growth.

EXAMPLE 2

DNA Sequence Analysis of DmORF1

Plasmids that confer suppression of the potassium-dependent phenotype are subjected to automated DNA sequence analysis performed by high temperature cycle sequencing (Applied Biosystems). Geneworks DNA sequence analysis software (Intelligenetics) is used to align raw DNA sequence information and to identify open reading frames. The DNA sequence of the 2.4 kb insert in pDmORF1 is displayed in SEQ. ID NO.:1. The 5' untranslated sequences of the cDNA contain long poly A and poly T tracts not likely to be found in protein coding regions. The first ATG proximal to the 5' end is present in a consensus *Drosophila melanogaster* translational initiation site [D. R. Cavener *Nucleic Acids Res.*, 15, 1353–1361 (1987)], consistent with the designation of this site as the translational start site. A single long open reading frame sufficient to encode a protein of 618 amino acids (predicted MW 68 kDa) is encoded in pDmORF1. A consensus polyadenylation site, AATCAA, occurs at position 2063–2068 in 3' untranslated sequences. The DmORF1 contains structural features that distinguish it from other classes of potassium channels, including four hydrophobic domains capable of forming transmembrane helices (M1–M4) and two pore forming H5 domains found between transmembrane helices M1 and M2, and M3 and M4. Each pore forming H5 domain contains the Y/F-G dipeptide motif required for potassium selectivity [L. Heginbotham, T. Abramson, R. MacKinnon, *Science* 258, 1152–1155, (1992)].

EXAMPLE 3

Identification of *Caenorhabditis elegans* Sequences Homologous to DmORF1

A search of the GENBANK database protein sequences similar to DmORF1 reveals significant matches with several known potassium channel sequences. The closest match is to a putative protein coding DNA sequence, F22b7.7, reported in the *Caenorhabditis elegans* genome sequencing project [R. Wilson, R. Ainscough, K. Anderson, et al., *Nature* 368, 32–38 (1994)]. The DNA sequence and predicted amino acid sequence assembled from putative exons recognized by a GENBANK exon identification algoritban is displayed in SEQ. ID. NOS:3 & 4. The DNA sequence contains a single long open reading frame sufficient to encode a protein of 336 amino acids (predicted MW 38.5 kDa) with substantial homology to known potassium channel sequences. The F22b7.7 sequence contains structural features that distinguish it from other classes of potassium channels, including three of four hydrophobic domains capable of forming transmembrane helices (M1–M4) identified in DmORF1 and two pore forming H5 domains found between transmembrane helices a predicted M1 and M2, and M3 and M4. Each pore forming H5 domain contains the Y/F-G dipeptide motif required for potassium selectivity [L. Heginbotham, T. Abramson, R. MacKinnon, *Science* 258, 1152–1155, (1992)]. The lack of an amino terminal transmembrane domain homologous to DmORF1 M1 in the F22b7.7 sequence may be due to failure of the search algorithm to identify exon(s) encoding the amino terminus. Alternatively, an amino terminal coding sequence may be added by trans-splicing, which occurs frequently in *Caenorhabditis elegans*.

EXAMPLE 4

Cloning and DNA Sequence Analysis of CeRF1

Oligonucleotides corresponding to DNA sequences encoding the two pore forming domains of F22b7.7 were synthesized using an Applied Biosystems DNA synthesizer.

F22b7.7-H2-1 nucleotides 97–147 of Seq. ID No.:3:
5'TCCATTTTCTTTGCCGTAACCGTCGT-
CACTACCATCGGATACGGTAATCCA.

F22b7.7-H2-2 nucleotides 490–540 of Seq. ID No.3 :
5'TCATTCTACTGGTCCTTCATTACAAT-
GACTACTGTCGGGTTTGGCGACTTG.

The oligos were labelled at their 5' ends with $^{32}P$ using a 5'-end labelling kit according to manufacturers instructions (New England Nuclear). The labelled oligos are pooled and used to screen $6\times10^5$ plaques from a λZAP-*Caenorhabditis elegans* cDNA library (obtained from Clontech) by published methods [T. N. Davis and J. Thorner *Meth. Enzymol.* 139, 246–262 (1987)]. Hybridization is at 42° C. for 16 hours. Positive clones are plaque-purified by twice repeating the hybridization screening process. Plasmid DNAs, excised from phage DNA according to manufacturers instructions, are subjected to automated DNA sequence analysis performed by high temperature cycle sequencing (Applied Biosystems). Geneworks DNA sequence analysis software (Intelligenetics) is used to align raw DNA sequence data and to identify open reading frames.

EXAMPLE 5

Functional Expression of a Rat Atrial Delayed Rectifier Potassium Channel in Yeast CY162 transformants containing plasmids pKAT1, which encodes a plant inward rectifier potassium channel, pRATRAK, which encodes a rat atrial delayed rectifier potassium channel, pDmORF1, and control plasmid pYES are cultured on arginine-phosphate-dextrose agar medium lacking ura medium [A. Rodriguez-Navarro and J. Ramos, *J. Bacteriol.* 159, 940–945, (1984)] containing various KCl concentrations. Strains containing pKAT1, pRATRAK, and pDmORF1 all support the growth of CY162 on medium containing a low concentration of potassium, while pYES2 containing CY162 cells only grow on medium containing a high potassium concentration, indicating that heterologous potassium channels of several different types function to provide high affinity potassium uptake.

pRATRAK is constructed by modifying the protein-coding sequences of RATRAK to add 5' HindIII and 3' XbaI sites using PCR. In addition, four A residues are added to the sequences immediately 5' proximal to the initiator ATG to provide a good yeast translational initiation site. The modified fragment is cloned into the HindIII and XbaI sites in the yeast expression vector pYES2 (Invitrogen), forming pRATRAK.

EXAMPLE 6

Bioassay of Functional Expression of Heterologous Potassium Channels

Yeast strains dependent on heterologous potassium channels for growth should be sensitive to non-specific potassium channel blocking compounds. To test the potassium channel blocking properties of several compounds, a convenient agar plate bioassay is employed. Strains containing pKAT1, pRATRAK, pDmORF1, and pYES2 are plated in arginine-phosphate-dextrose agar medium lacking ura and containing various amounts of potassium chloride. Arginine-phosphate-dextrose medium is used to avoid interference from potassium and ammonium ions present in standard synthetic yeast culture medium. Sterile filter disks were placed on the surface of the agar and saturated with potassium channel blocking ions CsCl, $BaCl_2$, and TEA. The growth of heterologous potassium channel containing strains is inhibited by in a channel dependent manner by potassium channel blocking ions. DmORF1-dependent growth is blocked by $BaCl_2$ but not by CsCl or TEA. KAT-dependent growth is blocked by $BaCl_2$, CsCl and TEA. RATRAK-dependent growth is blocked by $BaCl_2$, CsCl and TEA to a much greater extent than pKAT1, reflecting in part a slower growth rate of pRATRAK-containing cells. These observations confirm that these channels support the growth of the mutant yeast cells and demonstrate the efficacy of the yeast bioassay for screening for compounds that block potassium channel function. The control pYES-containing strain grows only around applied KCl and RbCl, a congener of KCl.

EXAMPLE 7

Identification of Compounds That Alter Potassium Channel Activity

Yeast strains made capable of growing on medium containing low potassium concentration by expression of heterologous potassium channels are used to screen libraries of chemical compounds of diverse structure for those that interfere with channel function. CY162 cells containing pKAT1, pRATRAK, pDmORF1, pCeORF1, and pYES2-TRK1 ($10^4$/ml) are plated in 200 ml of arginine-phosphate-dextrose agar medium lacking ura and containing 0.2 mM potassium chloride in 500 $cm^2$ plates. The CY162 cells bearing pYES2-TRK1 are included in the assay as a control to identify compounds that have non-specific effects on the yeast strain and are therefore not specifically active against the heterologous potassium channels. Samples of chemical compounds of diverse structure (2 ml of 10 mg/ml solution in DMSO) are applied to the surface of the hardened agar medium in a 24×24 array. The plates are incubated for 2 days at 30° C. during which time the applied compounds radially diffuse into the agar medium. The effects of applied compounds on strains bearing heterologous potassium channel genes are compared to the pYES2-TRK1 bearing strain. Compounds that cause a zone of growth inhibition around the point of application that is larger on plates containing cells bearing the heterologous potassium channels than that observed around the pYES2-TRK1 bearing strains are considered selective potassium channel blockers. Compounds that induce a zone of enhanced growth around the point of application that is larger on plates containing cells bearing the heterologous potassium channels than that observed around the pYES2-TRK1 bearing strains are considered selective potassium channel openers.

What is claimed is:

1. An isolated nucleotide sequence comprising the nucleotide sequence of Seq. I.D. No. 1.

2. An isolated nucleotide sequence encoding an amino acid sequence of Sequence I.D. No. 2.

3. An expression vector capable of expressing a heterologous, potassium channel in a cell membrane of a yeast cell comprising the nucleotide sequence of claim 1.

4. An expression vector capable of expressing a heterologous potassium channel in a cell membrane of a yeast cell comprising the nucleotide sequence of claim 2.

5. The expression vector of claims 3 or 4 which is selected from the group consisting of pYES2, pAD4M, pPGKH, YEp52 or pYSK153.

6. A transformed yeast cell comprising the nucleotide sequences of claims 1 or 2.

7. A transformed yeast cell comprising the expression vector of claims 3, 4 or 5.

* * * * *